United States Patent [19]
Krietemeier et al.

[11] Patent Number: 4,713,164
[45] Date of Patent: Dec. 15, 1987

[54] APPARATUS FOR ANALYZING MALODORS IN THE BREATH

[75] Inventors: Rickie F. Krietemeier, Englewood; Laurence W. Ross, Denver, both of Colo.

[73] Assignee: Confidence Corporation, Englewood, Colo.

[21] Appl. No.: 758,826

[22] Filed: Jul. 25, 1985

[51] Int. Cl.⁴ ............................................ G01N 27/46
[52] U.S. Cl. .................................. 204/400; 204/1 T; 204/431; 204/432
[58] Field of Search ............... 204/1 T, 1 F, 431, 432, 204/400

[56] References Cited

U.S. PATENT DOCUMENTS

| | | | |
|---|---|---|---|
| Re. 31,915 | 6/1985 | Oswin et al. | 204/432 |
| 3,088,905 | 5/1963 | Glover | 204/415 |
| 3,223,608 | 12/1965 | Hersch | 204/431 |
| 3,269,924 | 8/1966 | Nessler | 204/431 |
| 3,296,113 | 1/1967 | Hansen | 204/432 |
| 3,342,558 | 9/1967 | Reinecke | 204/432 |
| 3,493,484 | 2/1970 | Berg et al. | |
| 3,494,838 | 2/1970 | Chapron et al. | 204/431 |
| 3,755,800 | 8/1973 | Purt . | |
| 3,852,169 | 12/1974 | Kring et al. | 204/432 |
| 4,042,464 | 8/1977 | Blurton et al. | |
| 4,051,006 | 9/1977 | Neti et al. | |
| 4,063,898 | 12/1977 | Fisher . | |
| 4,169,779 | 10/1979 | Tataria et al. | 204/415 |
| 4,333,810 | 6/1982 | Wolcott et al. | |
| 4,364,810 | 12/1982 | Razumney . | |

Primary Examiner—T. Tung
Attorney, Agent, or Firm—John E. Reilly

[57] ABSTRACT

In sensing diluent gases which contribute to malodors in the human breath, a detection cell is housed within the hand-held cartridge made up of inner and outer casings movable between and open and closed position. The detection cell has an electrolyte interposed between inner and outer electrodes within the inner casing and when the cartridge is advanced to its open position a sample gas stream created by blowing into the interior of the cartridge is passed into contact with the inner electrode while a reference gas stream, such as, air contacts the outer electrode whereby an electric potential is developed in response to the presence of the diluent gases indicating the presence of malodors in the human breath.

13 Claims, 3 Drawing Figures

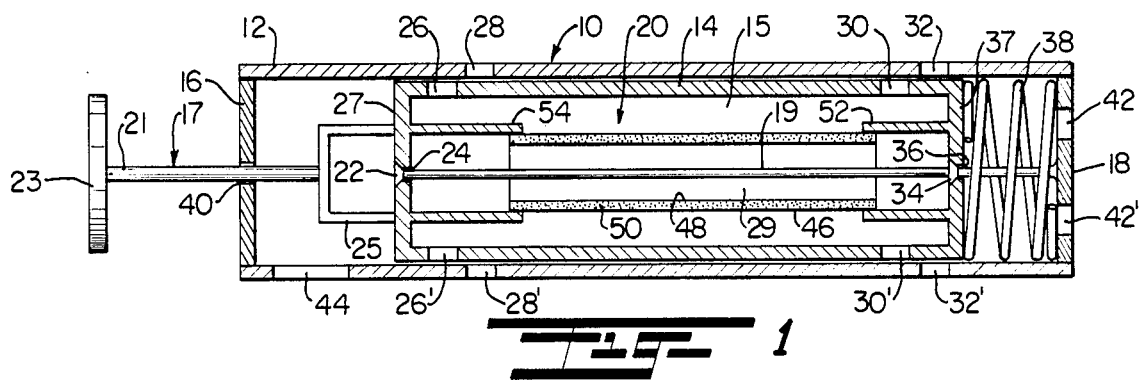
_Fig. 1_
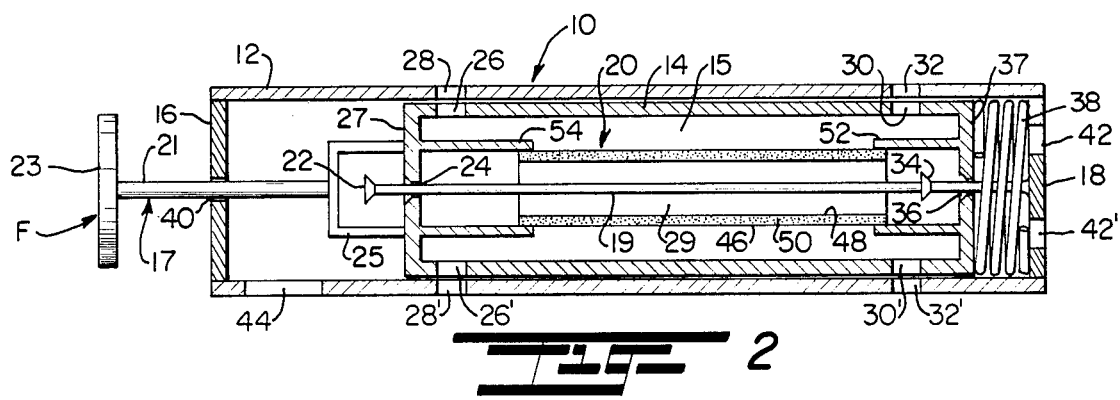
_Fig. 2_
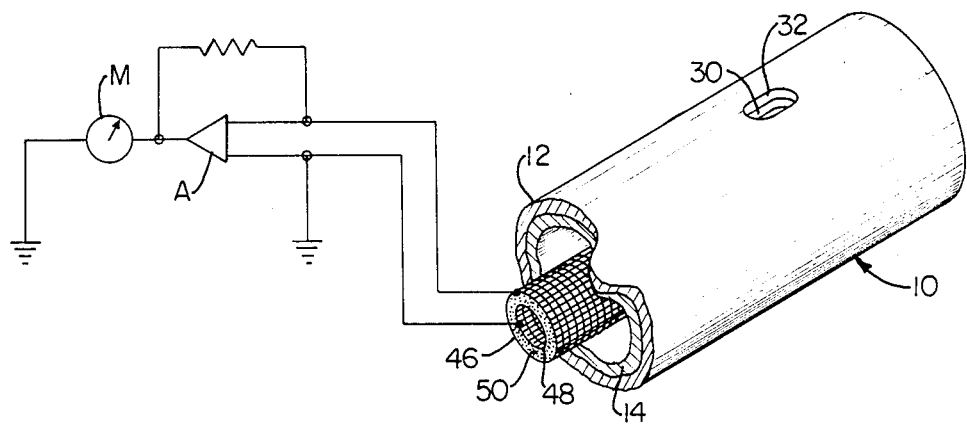
_Fig. 3_

APPARATUS FOR ANALYZING MALODORS IN THE BREATH

The present invention relates to a novel and improved apparatus for analyzing malodors in the breath; and more particularly relates to a novel and improved portable sensing unit and method for rapidly detecting diluent gases, such as, those which contribute to malodor in the human breath.

BACKGROUND AND FIELD OF THE INVENTION

Hydrogen sulfide ($H_2S$) and methyl mercaptan ($CH_3SH$) are well-known to be the principal contributors to oral malodor. Both compounds arise from degradation of various substances in the mouth through the action of oral microorganisms. The quantity of hydrogen sulfide present in the human breath is typically about three times that of methyl mercaptan.

Hydrogen sulfide in gas streams or the atmosphere may be determined by a number of scientific methods of measurement. The standard method for determining the concentration of $H_2S$ in the ambient atmosphere involves passing a sample through a suspension of cadmium hydroxide, $Cd(OH)_2$, followed by reaction with P-amino-N,N-dimethylaniline to form methylene blue. The most widely used apparatus for detection of $H_2S$ operates by passing the gas stream through a paper tape impregnated with lead acetate, mercuric chloride, silver nitrate or potassium dicyanoargentate with the concentration of $H_2S$ being measured as a function of the optical density of the resulting metal sulfide precipitate. Other methods, including titration methods, gas chromatography, chemiluminescence, and semi-conductor surface alteration may be used. However, all of these methods are cumbersome, slow or demanding in other respects.

To achieve the two principal goals of small size and fast response, an electrochemical method offers the only practical alternative. Such a method is based on the oxidation of $H_2S$ at the anode and the simultaneous reduction of hydrogen at the cathode to yield a flux of electrons through a closed circuit from anode to cathode. The electrode reactions are as follows:

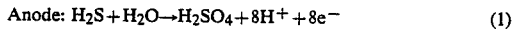

Anode: $H_2S + H_2O \rightarrow H_2SO_4 + 8H^+ + 8e^-$ (1)

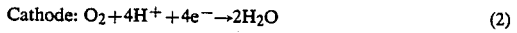

Cathode: $O_2 + 4H^+ + 4e^- \rightarrow 2H_2O$ (2)

These reactions may be catalyzed by use of electrodes which are constructed of catalytic materials, such as, noble metals. The combination of reactions (1) and (2) yields the overall reaction: $H_2S + 2O_2 \rightarrow H_2SO_4$. These reactions are intrinsically rapid when they are properly catalyzed, but they can proceed only as rapidly as the material to be oxidized ($H_2S$) reaches the anode.

Previous devices based on electrochemical methods have employed so-called diffusion electrodes, which typically depend on the use of a permeable film of polymeric material, e.g., TEFLON ®, for the purpose of retaining the liquid electrolyte solution while permitting the diffusion of gas through the permeable film. Use of such a film is intended to retard loss of water or other electrolytic solvent by evaporation. However, the film also retards the rate at which the gas is able to reach the electrode. The result is a retardation of the response time of the device as a whole.

The purpose of the permeable film in previous inventions is to regulate the concentration of the electrolyte solution such that this concentration remains essentially constant. In particular, the loss of water due to migration of moisture in and out of the electrolyte solution is suppressed by use of a gas-permeable, hydrophobic membrane for the permeable film. Such a membrane has a pore structure which permits the diffusion of gas inward into the electrolyte solution, but its hydrophobic nature supresses the migration of water outward from the electrolyte solution.

One measure proposed to prevent the loss of water from the electrolyte solution is the use of humectant substances dissolved in the electrolyte solution. Another measure proposed is the use of a solid electrolyte instead of a liquid. Such a solid electrolyte may be a completely solid matrix or a rigid aqueous gel. Still another measure to compensate for the tendency of an aqueous electrolyte to lose or gain water and thus change its composition is the use of buffering chemicals in the electrolyte solution. In addition, this measure will compensate for any alteration in an electrolyte solution pH due to variation of the strength of the electrolyte.

U.S. Pat. No. 4,169,779 to Tataria et al describes an electrochemical cell for the detection of hydrogen sulfide. This cell is constructed with the explicit intention of avoiding the use of an aqueous electrolyte because of the sensitivity of such an electrolyte to the humidity in the air. Instead of an aqueous electrolyte, the cell employs an electrolyte which consists of lithium perchlorate or other inorganic salt dissolved in an organic solvent. The cell has a low detectability level for hydrogen sulfide, but has a very slow response time (e.g., up to six minutes to achieve 90% of maximum reading).

The main disadvantages of the gas sensors described in the prior art, namely, slow response and limited shelf life, are overcome in accordance with the present invention by maintaining the solution in a sealed condition when not in use so as to avoid the need for a permeable film which shields the electrolyte solution from direct contact with the gas. Specifically, in the present invention the gas dissolves in the aqueous electrolyte solution in the immediate vicinity of the electrode without the interference of an intermediate film. This feature greatly accelerates the rate at which the gases at the respective electrodes can enter into the reactions described above to within a matter of seconds. At the same time, it is desirable to provide an extremely compact, lightweight container which is normally sealed to prevent loss of the solution through evaporation and can be stored in a pocket or purse so as to be readily available for use in detecting malodor in the human breath.

SUMMARY OF THE INVENTION

It is an object of the present invention to provide a novel and improved sensor for the detection of gaseous constituents of the human breath which indicate the presence of malodor or bad breath.

It is another object of the present invention to provide a sensor for the rapid detection of low molecular weight compounds of sulfur in the human breath.

Still another object of the present invention is to provide a novel and improved sensor for the detection of gaseous constituents of the human breath which is compact, lightweight and portable so as to be conveniently carried on one's person.

A further object of the present invention is to provide a housing for a gaseous sensor which is normally closed when not in use in order to preserve the operative components of the sensor and which when opened will enable the components to rapidly respond to the presence of gaseous constituents and provide a measurement of same.

Yet another object of the present invention is to provide a novel and improved method for detecting and indicating the presence of low molecular weight compounds of sulfur in the human breath in a reliable and effective manner.

In accordance with the present invention, an improved sensor for the detection of contaminants in streams of diluent gases by electrochemical methods comprises means defining a normally sealed, hand-held housing having an open position and a closed position. A detection means is disposed within the housing and comprises at least two electrodes and an electrolytic means, the electrolytic means being in communication with the electrodes and operable to create an electric potential between the electrodes upon detection of contaminants in sample gas streams. First and second valve means are provided for selectively directing a sample gas stream to one electrode and for selectively directing a reference gas stream to the other electrode with the housing in an open position. Means are provided for producing an electric signal upon detection of contaminants by the detection means.

In accordance with the above-mentioned objectives, a method for detecting and indicating the presence of contaminants in the human breath comprises the steps of mounting a detection means in a normally sealed housing; opening the housing and directing a reference gas stream to one electrode of the detection means and directing a sample gas stream to the other electrode of the detection means; reacting the gaseous constituents of the reference and sample gas streams with the electrodes of the detection means to develop an electric potential in response to the presence of gaseous contaminants; and producing a signal proportional to the electric potential generated to indicate the presence of gaseous contaminants in the housing.

The above and other objects, advantages and features of the present invention will become more readily appreciated and understood from the foregoing detailed description of preferred and alternate embodiments when taken together with the accompanying drawings, in which:

BRIEF DESCRIPTION OF THE DRAWINGS

FIG. 1 is a sectional view of a preferred embodiment of the present invention showing the housing in the closed position;

FIG. 2 is a sectional view of the present invention corresponding to FIG. 1 and showing the housing in the open position; and FIG. 3 is a perspective view of the detection means in the housing and schematically illustrating one form of signal generating circuit.

DETAILED DESCRIPTION OF THE PREFERRED EMBDODIMENT

In a preferred embodiment of the present invention a portable housing or cartridge 10 is shown generally in its open position in FIG. 1 and in its closed position in FIG. 2. The housing 10 comprises a generally cylindrical outer casing 12 and a generally cylindrical inner casing 14, the inner casing being received in close-fitting, inner concentric, slidable relation to the outer casing 12 so as to be movable therein. A detection cell 20, described in greater detail hereinbelow, is mounted in inner concentric relation to the inner casing 14.

The circumferential sidewall of the outer casing 12 includes a sample gas stream intake aperture 44 and diametrically opposed reference gas stream apertures 28, 28', 32, and 32' adjacent to opposite ends of the outer casing. One end wall 18 of the outer casing 12 includes exhaust apertures 42 and 42'; and an opposite actuator end wall 16 of the outer casing 12 includes a centrally disposed bore 40 adapted to receive shaft 21 of actuator 17 in close-fitting relationship so as to prevent passage of gas streams therethrough.

The inner casing 14 includes opposite end walls 27 and 37 provided with intake aperture or valve seat 24 and exhaust aperture or valve seat 36, respectively, which are centrally disposed and axially aligned with one another. Diametrically opposed reference gas stream apertures 26, 26', 30 and 30' are located in the circumferential sidewall wall of inner casing 14 adjacent to opposite ends thereof and are spaced so as to be alignable with corresponding reference gas stream apertures in the circumferential sidewall wall of outer casing 12 when the housing is advanced to the open position. In the discussion below, reference will be made to aligned aperture pairs 26, 28 and 30, 32 in discussing the alignment of the reference gas stream apertures. It is to be understood that any reference to the aforementioned aperture pairs shall apply also to aperture pairs 26', 28' and 30', 32' even though the latter are not explicitly referred to.

As may be seen in FIGS. 1 and 2, a generally tubular detection cell 20 is mounted within inner casing 14. The detection cell comprises an anode 48, a cathode 46 and an electrolyte media 50. The anode 48 and cathode 46 form the inner and outer walls, respectively, of the detection cell. The electrolyte media 50, described in greater detail hereinafter, is interposed between the anode 48 and cathode 46. The anode 48 and cathode 46 each is in the form of a grid or screen, as may be seen in FIG. 3, comprising a suitable electrode material, such as, a noble metal.

The electrolyte solution employed in the preferred embodiment of the present invention is a solution of sulphuric acid or other mineral acid. The solution is contained within the electrolyte media 50 which is in the form of a thin strip of absorbent material, such as, felt, gauze or mesh. The layer of electrolyte media in the present invention is very thin and the electrolyte solution contained therein is protected from dehydration by the closable housing which isolates the detection cell from contact with the atmosphere when not in use.

The detection cell 20 is secured within the inner casing 14 by means of generally tubular mounting collars 54 and 52 which are attached to the interior walls of intake end 27 and exhaust end 37, respectively, of inner housing 14, the collars 52 and 54 having open ends disposed in axially spaced, facing relation to one another. As may be seen in FIGS. 1 and 2, the inner diameter of the tubular collars 52 and 54 is equal to the outer diameter of the detection cell 20. The detection cell 20 is secured within the inner casing by frictional engagement between opposite ends of the outer surface of anode 46 and the inner surfaces of collars 52 and 54. With the detection cell mounted as described above, the inner casing 14 is divided into an outer annular chamber 15 adapted to receive reference gas streams, and an inner chamber 29 adapted to receive sample gas streams.

A valve support shaft 19 is attached to the interior surface of end wall 18 of the outer casing 12 and extends along a central longitudinal axis through the valve seats 24 and 36 in the casing 12 to terminate in an intake valve 22 which is attached to the distal end of shaft 19. An exhaust valve 34 is attached to shaft 19 at a point inwardly of the end wall 37, as shown in FIGS. 1 and 2.

In order to retain the inner casing 14 in a normally closed or sealed position with respect to the outer casing 12, a spring member 38, in the form of a helical coil, is interposed in the exhaust end of outer casing 12 to exert a biasing force urging the inner casing 14 to the closed position, as shown in FIG. 1. With the casing 14 in the closed position, the apertures in the circumferential sidewalls of inner and outer casing 14 and 12 are axially offset to prevent passage of reference gas streams into the chamber 15 of inner casing 14. Furthermore, gas streams are prevented from entering the interior of detection cell 20 by the valves 22 and 34 which seal intake and exhaust seats 24 and 36, respectively, in the end walls of inner casing 14.

The biasing force of the helical coil member 38 may be overcome by applying a manual force F to actuator 17 thereby moving the inner casing 14 to the open position shown in FIG. 2. The actuator 17 comprises a plunger having a disc-shaped, enlarged head 23, a shaft 21 received through aperture 40 in the actuator end 16 of the outer casing 12 and a U-shaped mounting bracket 25 attached to the outer surface of intake end 27 of the inner casing 14. As seen in FIG. 2, the mounting bracket 25 provides clearance between the actuator 17 and valve member 22 with the casing 14 in the open position.

When the inner casing 14 is advanced to the open position by depressing the plunger, as shown in FIG. 2, the reference gas stream aperture pairs 26, 28 and 30, 32 in the circumferential walls of inner casing 14 and outer casing 12 are aligned to form passages for a reference gas stream to enter chamber 15 of inner casing 14 and to come into contact with the anode 46 of detection cell 20. A sample gas stream is directed to the interior of the detection cell by the passage provided through intake aperture 44 in outer casing 12 and through the annular valve seat 24 in inner casing 14. An exhaust passage is provided through the annular valve seat 36 in inner casing 14 and through exhaust apertures 42, 42' in outer casing 12.

The cartridge 10 of the present invention is operated by applying a manual force F to the head 23 of actuator 17, thereby transmitting a force to the inner casing 14 to overcome the biasing force of spring member 38 and to move the housing into the open position, as shown in FIG. 2. The user then directs a stream of sample gas by blowing into the interior chamber 29 of detection cell 20 via the pathway provided by intake apertures 44 and 24 of outer casing 12 and inner casing 14, respectively. In the open position, a reference gas stream, free of the contaminating constituent and consisting mostly or entirely of air, is allowed to enter through aligned port pairs 28, 26 and 30, 32 into chamber 15 and is directed to the cathode 46 of the detection cell 20. The respective gas streams proceed to contact the electrolyte solution by passing through the pores in the electrodes 46 and 48. A small fraction of the total volume of sample gas which enters the interior chamber 29 of the detection cell 20 diffuses through the electrolyte media 50. The combination of the sample gas entering the electrolyte media 50 from chamber 29 in the interior of the detection cell 20 and ambient air which enters through chamber 15 via aligned port pairs 26, 28 and 30, 32 initiates reactions (1) and (2), described hereinabove, thus creating an electric potential between the cathode 46 and anode 48 of the detection cell 20. This potential is amplified by an amplifier A connected to the electrodes of detection cell 20 and displayed on a meter M to provide an analog representation of the presence of contaminants in the sample gas stream.

The present invention operates on the principle of a simple electrochemical detection cell employing a strong acid electrolyte in combination with catalytic electrodes. Such a system is common in the branch of electrochemistry known as "fuel cell" technology. In the present invention, the gas stream containing the contaminating constituent, e.g. $H_2S$, is directed to the anode of the detection cell, while a reference gas stream, free of the contaminating constitutent and consisting mostly or entirely of air, is directed to the cathode of the detection cell.

The reactions (1) and (2) occur because there is an oxidizable material at the anode and an oxidant at the cathode. As the reactions progress, excess electrons are created at the anode and consumed at the cathode, thus creating an electric current between the electrodes. The electric current ceases when the oxidizable constituent in the volume of gas delivered to the anode is completely oxidized, for example, when $H_2S$ is oxidized to $H_2SO_4$.

In most applications of fuel cell technology, the objective is to generate the maximum electric current possible per unit volume of the system. Systems directed to this objective typically operate at slower rates and have an electrochemical cell which is exposed to the atmosphere for long periods of time, thus requiring a gas-permeable film to protect the electrolyte from dehydration. By contrast, the objective of the present invention is not maximum current generation, but rapid generation of a threshold current indicating the presence of contaminants in a gas stream. The electrolyte layer in the present invention, therefore, is held as thin as possible to maximize the rate at which reactants reach the electrodes. Furthermore, the electrolyte layer is not enclosed in a gas-permeable membrane because such a membrane would also slow the reaction. Indeed, such a membrane is not necessary in the present device because the electrolyte is protected from dehydration by the normally sealed housing.

An experiment utilizing the detection cell of the present invention for the detection of malodors in the human breath was carried out as follows: An electrolytic cell was assembled using electrodes formed from identical discs of 100 mesh copper wire screen, about 1" in diameter, upon which had been electroplated a layer of gold and then a layer of platinum black. The electrolyte zone, inserted between the electrodes consisted of a pad of cotton cloth which was impregnated with a solution of 28% sulfuric acid. The assembly was pressed together between rectangular pieces of composite board, with holes cut in the board in order to allow gas contact with both electrodes. The electrodes were connected by attached wires to terminals of a Fluke Model 8050A digital voltmeter with an impedance of about 10 meghoms.

Under undisturbed conditions, the numerical reading was an average of 2.5±0.1. Manual pressure was applied to the electrodes, with no observed change in the indicated value. When the observer blew his breath upon one of the electrodes, the reading at the indicating face of the voltmeter increased to about 3.0 within a matter of a few seconds. This was repeated several times. The reading dropped back to about 2.5 when the contact with the breath was ceased.

It is therefore to be understood that various modifications and changes may be made in the construction and arrangement of parts comprising the various embodiments of invention as described herein without departing from the spirit and scope of the invention as defined by the appended claims and reasonable equivalents thereof.

We claim:

1. A sensor for the detection of contaminants in streams of gases by electrochemical methods, the combination comprising:
   means defining a normally sealed, hand-held housing including inner and outer casings movable between an open position and a closed position;
   detection means operably disposed within said housing, said detection means comprising at least two electrodes and electrolyte means, said electrodes in communication with said electrolyte means, said electrolyte means operable to create an electric potential between said electrodes upon detection of contaminants in a sample gas stream;
   first valve means for selectively directing a sample gas stream to one of said electrodes with said housing in the open position;
   second valve means for selectively directing a reference gas steam to another electrode with said housing in the open position; and
   means for producing an electic signal upon detection of contaminants by said detection means.

2. A sensor according to claim 1, said inner casing disposed in close-fitting, inner concentric relation within said outer casing and movable therein between a first position, wherein said housing is in said open position, and a second position, wherein said housing is in said closed position.

3. A sensor according to claim 2, said outer casing and said inner casing being generally cylindrical in shape.

4. A sensor according to claim 3, said housing further comprising means biasing said inner casing toward said second position.

5. A sensor according to claim 4, said biasing means comprising a helical spring member interposed between one end of said inner casing and one end of said outer casing.

6. A sensor according to claim 5, said inner casing including actuator means at an end of said inner casing opposite to said one end, said actuator means operative to overcome said biasing means in advancing said inner casing to said first, open position.

7. A sensor according to claim 6, said detection means being of slender, elongated tubular configuration, and mounting collar means at opposite ends of said inner casing for mounting said detection means within said inner casing, said detection means having inner and outer concentric layers defining said two electrodes.

8. A sensor according to claim 7, said electrodes being in the form of a wire grid composed of a noble metal, and said electrolyte means defined by a layer of absorbent material containing a liquid electrolyte composed at least in part of a mineral acid, said electrolyte means being interposed between said two electrodes.

9. A sensor unit for the detection of malodors in the human breath comprising in combination:
   a hand-held cartridge including an inner casing and outer casing, said inner casing disposed in inner concentric relation to said outer casing and movable therein between open and closed positions;
   detection means disposed within said inner casing, said detection means having inner and outer concentric electrodes and an electrolyte media therebetween, said electrolyte media operative to create an electric potential between said electrodes upon detection of contaminant gases in a sample gas stream introduced into contact with said inner electrode;
   first valve means operative to form a passageway through said inner casing for admission of the human breath through an aperture in said outer casing into contact with said inner electrode when said cartridge is in the open position;
   second valve means for selectively directing a reference gas stream into contact with said outer electrode when said housing is in the open position; said second valve means defined by apertures in said inner and outer casing movable into alignment with one another in response to relative movement between said inner and outer casings to the open position; and
   means for producing an electrical signal in response to detection of contaminant gases in the human breath.

10. A sensor according to claim 9, including biasing means normally urging said inner casing to the closed position with respect to said outer casing, said biasing means defined by a spring member interposed between adjacent ends of said inner and outer casings.

11. A sensor according to claim 10, including an actuator member projecting from an end of said inner casing opposite to said adjacent ends through a bore in said outer casing.

12. A sensor according to claim 9, said detection means being of elongated, slender tubular configuration with said electrolyte media interposed between said inner and outer electrodes, and axially spaced end support means for supporting opposite ends of said detection means within said inner casing.

13. A sensor according to claim 9, including exhaust apertures in one end of said inner and outer casings, said exhaust aperture in said one end of said inner casing being normally closed by said first valve means and movable to the open position in response to relative movement between said inner and outer casings to the open position.

* * * * *